(12) United States Patent
Hotchkiss et al.

(10) Patent No.: US 6,592,538 B1
(45) Date of Patent: Jul. 15, 2003

(54) DYNAMIC ORTHOPEDIC BRACES

(75) Inventors: Robert N. Hotchkiss, Riverside, CT (US); Bruce H. Robie, New York, NY (US); Mark A. Deitch, Timonium, MD (US); Mark W. Lenhoff, New York, NY (US); J. Chris Fritton, New York, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 0 days.

(21) Appl. No.: 09/044,914

(22) Filed: Mar. 20, 1998

(51) Int. Cl.$^7$ .................................................. A61F 5/00
(52) U.S. Cl. ........................................ 602/26; 602/21
(58) Field of Search .............................. 602/20, 21, 22, 602/13; 601/149–152

(56) References Cited

U.S. PATENT DOCUMENTS

| | | |
|---|---|---|
| 1,366,576 A | 1/1921 | Maddox |
| 1,860,995 A | 5/1932 | Collender |
| 2,357,323 A | 9/1944 | Goldberg |
| 2,767,708 A | 10/1956 | Keropian |
| 3,028,858 A | 4/1962 | Cutler |
| 3,124,127 A | 3/1964 | Ruuska |
| 3,707,963 A | 1/1973 | Keropian |
| 3,714,940 A | 2/1973 | Palmer |
| 3,769,970 A | 11/1973 | Swanson |
| 3,868,952 A | 3/1975 | Hatton |
| 3,937,215 A | 2/1976 | Barthlome |
| 4,274,399 A | 6/1981 | Mummert |
| 4,294,237 A | 10/1981 | Frazier |
| 4,440,159 A | 4/1984 | Cochran |
| 4,465,076 A | * 8/1984 | Sturgeon .................... 606/202 |
| 4,619,250 A | 10/1986 | Hasegawa |
| 4,671,258 A | 6/1987 | Barthlome |
| 4,677,971 A | 7/1987 | Lindemann |
| 4,807,606 A | 2/1989 | Hasegawa et al. |
| 4,941,460 A | 7/1990 | Working |
| 5,002,044 A | 3/1991 | Carter |
| 5,052,379 A | 10/1991 | Airy et al. |
| 5,112,296 A | 5/1992 | Beard et al. |
| 5,213,094 A | 5/1993 | Bonutti |
| 5,254,078 A | 10/1993 | Carter et al. |
| 5,259,369 A | 11/1993 | Matsumura et al. |
| 5,285,773 A | 2/1994 | Bonnutti et al. |
| 5,337,737 A | 8/1994 | Rubin et al. |
| 5,346,461 A | * 9/1994 | Heinz et al. .................. 602/19 |
| 5,358,469 A | 10/1994 | Patchel et al. |
| 5,358,471 A | 10/1994 | Klotz |
| 5,423,333 A | 6/1995 | Jensen et al. |
| 5,466,192 A | * 11/1995 | Castolo et al. ................ 473/62 |
| 5,514,081 A | 5/1996 | Mann |
| 5,601,597 A | 2/1997 | Arrowood et al. |
| 5,653,680 A | * 8/1997 | Cruz ........................... 602/21 |
| 5,728,055 A | * 3/1998 | Sebastian ..................... 602/19 |
| 5,891,061 A | * 4/1999 | Kaiser ......................... 601/33 |
| 2001/0020143 A1 | * 9/2001 | Stark et al. ................... 602/19 |

FOREIGN PATENT DOCUMENTS

| | | |
|---|---|---|
| SU | 596-236 | 8/1976 |
| WO | 9842257 | * 1/1998 |
| WO | WO 9842257 | 10/1998 |

* cited by examiner

Primary Examiner—Kim M. Lewis
(74) Attorney, Agent, or Firm—Morgan & Finnegan, LLP

(57) ABSTRACT

The present invention relates to a brace including a support member that is configured to the actual or desired shape of a user's body part, a support structure for mounting the support member on a user, a variable force applicator for adjusting the amount of force to be applied by the support member and an indicator for displaying the force applied.

66 Claims, 14 Drawing Sheets

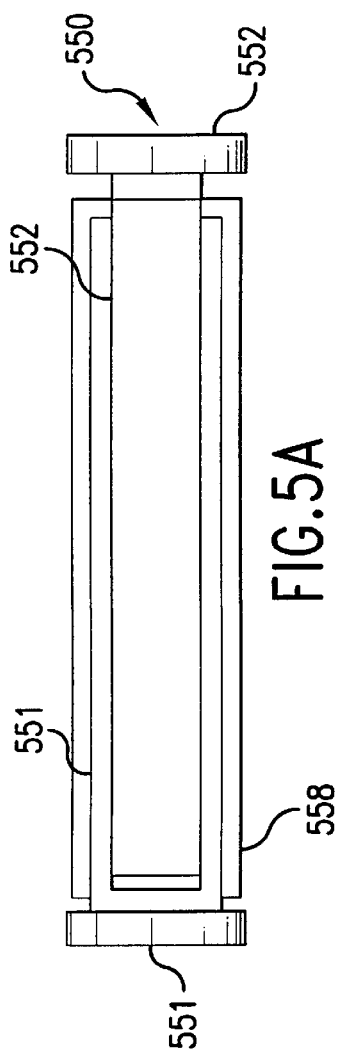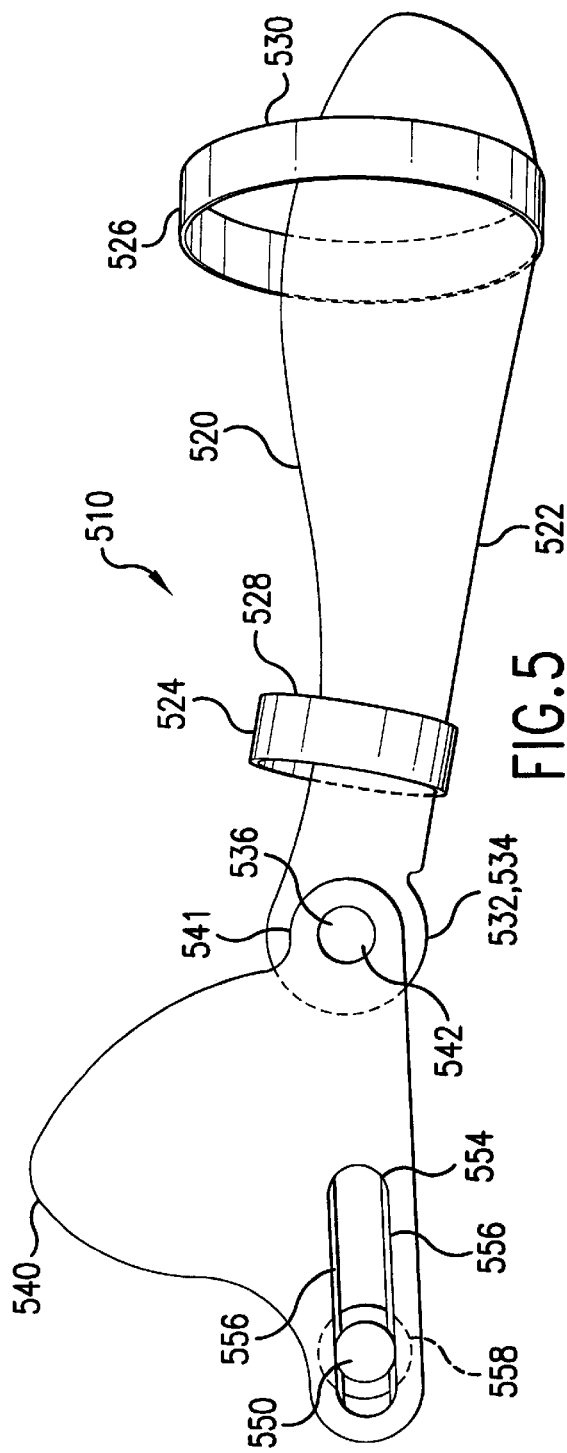

DYNAMIC ORTHOPEDIC BRACES

FIELD OF THE INVENTION

The present invention relates to orthopedic devices including a support member which is configured to the actual or desired shape of a user's body part and is removably attached to the user by a support structure. The support member includes a variable force applicator for adjusting and directly applying force to the user with an indicator for displaying the force applied. More specifically, the present invention relates to dynamic braces, and in particular to a "smart" dynamic wrist brace that reduces and maintains the reduction of extra articular fractures of the distal radius by applying a palmarly directed force to the metacarpals and distal carpus.

BACKGROUND OF THE INVENTION

Orthopedic braces for immobilizing or providing limited movement of the hand and/or wrist, to allow for healing, are known, and include conventional and dynamic types of braces. For example, U.S. Pat. No. 2,767,708 to Keropian relates to an orthopedic hand brace having a forearm support which is pivotally connected to the hand support, whereby lateral movement of the hand brace is possible.

In U.S. Pat. No. 5,002,044 to Carter, the distal ends of struts which form part of the forearm and hand assembly supports are connected at a rotation plate which limits rotation of the hand assembly support relative to the forearm assembly support. The proximal ends of the struts may be slidably received within sleeves and coact with tension or compression springs.

In U.S. Pat. No. 5,254,078 to Carter, the wrist brace includes a palmar and dorsal hand support. Dorsal pressure is applied to the hand through an inclined lateral support which is integral with a lateral extension that is pivotally connected to the arm assembly.

In U.S. Pat. No. 5,358,469 to Patchel, a dynamic wrist splint is described in FIGS. 16–19, where hand and arm assemblies are pivotally connected to one another. The dynamically adjustable force is provided by the flexible palmar strap and pad, and rotation of the strap relative to the palmar strap.

In the above devices, the inter-relationship of the varied parts is very complicated. Thus a need exists for a simplified orthopedic device. Also, the above exemplified devices do not provide an adjustable, palmarly directed force with automatic feedback on the amount of force applied to fix the fracture, with the intent that the displacement can be adjusted so as to generate the appropriate amount of force.

SUMMARY OF THE INVENTION

The present invention relates to an orthopedic brace which provides the automatic feedback on the amount of force applied to maintain or reduce a fracture or to maintain or reduce a malalignment or to change alignment, so that the appropriate amount of force can be applied. The brace includes a first support member configured to fit a user's body part and is connected to releasable structure for attaching the brace to the user. The configured support member includes a variable force applicator to increase or decrease pressure/force applied to the user and an indicator for displaying the amount of force that is applied.

One object of the present invention is to provide an orthopedic brace with automatic feedback on the amount of force applied to a support member configured to fit a body part of a user and fix a fracture.

Another object of the present invention is to provide a wrist brace with palmarly directed force feedback.

Another object of the present invention is to provide a knee device with feedback on the amount of force being applied.

A still further objected is to provide a simplified brace that can be easily adjusted.

A further object of the present invention involves providing a method for maintaining or reducing a fracture or maintaining or reducing a malalignment, or changing the alignment, in response to the automatic feedback of the orthopedic brace of the present invention.

Objects and advantages of the invention are set forth in part herein and in part will be apparent herefrom, or may be learned by practice with the invention, the same being realized and attained by means of the structures, instrumentalities and combinations pointed out in the appended claims. Accordingly, the invention resides in the novel parts, structures, arrangements, combinations and improvements herein shown and described.

BRIEF DESCRIPTION OF THE DRAWINGS

FIG. 5 shows a side view of the first embodiment according to the present invention.

FIG. 5A is a cross-sectional view of the palmar support according to the present invention.

DETAILED DESCRIPTION OF THE INVENTION

The present invention relates to an orthopedic brace which provides the automatic feedback on the amount of force applied to maintain or reduce a fracture or to maintain or reduce a malalignment or to change alignment, so that the appropriate amount of force can be applied. The brace includes a first support member configured to fit a user's body part and is connected to releasable structure for attaching the brace to the user. The releasable structure is provided by Velcro® fasteners and Velcro® straps in a first embodiment. In a second embodiment, the straps for attaching the backbrace to the user are the releasable structure. In a third embodiment, the strap for the knee brace forms the releasable structure.

In a first embodiment of the present invention, a wrist brace is provided which is designed to treat non-articular fractures of the distal radius. The device provides automatic feedback on the amount of force applied to fix the fracture, with the intent that the displacement force can be adjusted so as to generate the appropriate amount of force.

The brace applies a palmarly directed force to the dorsum of the hand which maintains the reduction of the fracture, in a variety of wrist positions. The palmarly directed force is resisted at the forearm and at the distal aspect of the metacarpal row. At the same time, the bending moment induced by the palmarly directed force must be resisted by the forearm components with respect to the forearm.

Figure 1:
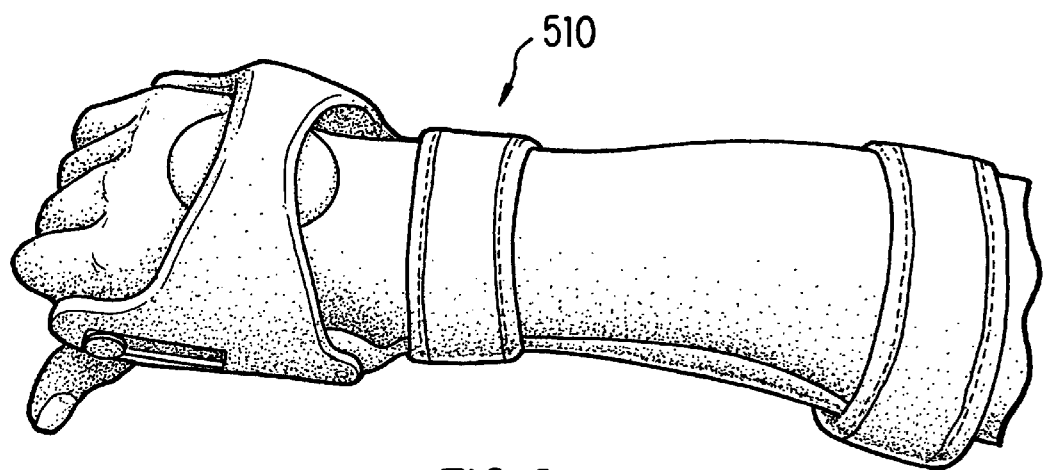
FIG. 1 shows a dorsal view of a first embodiment according to the present invention, on a user.
Figure 2:
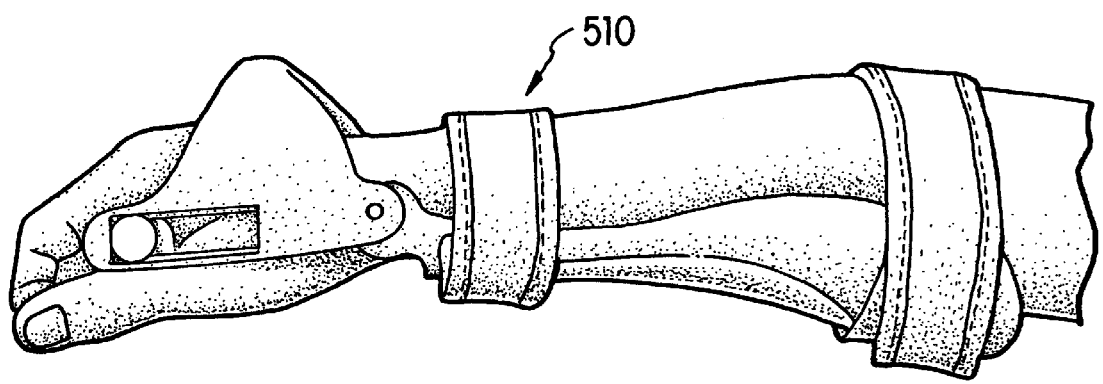
FIG. 2 shows a lateral view of the first embodiment according to the present invention, on a user.
Figure 3:
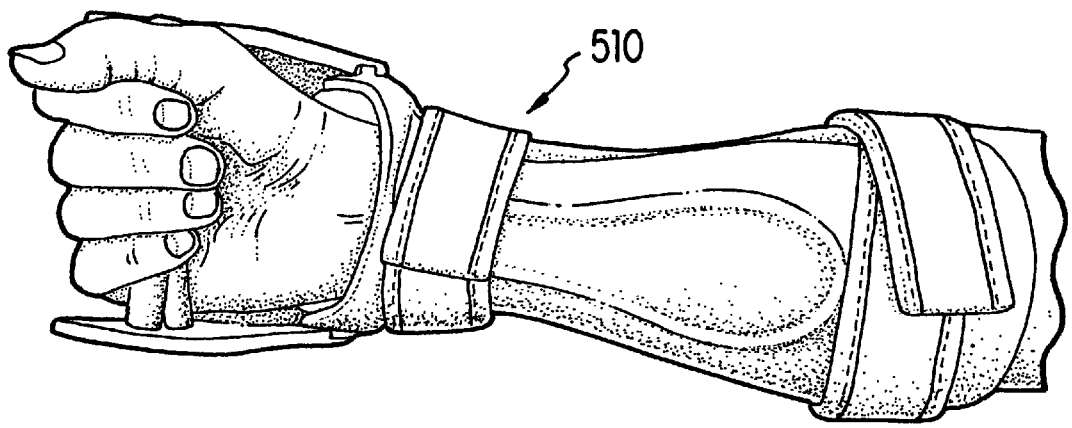
FIG. 3 shows a palmar view of the first embodiment according to the present invention, on a user.
Figure 4:
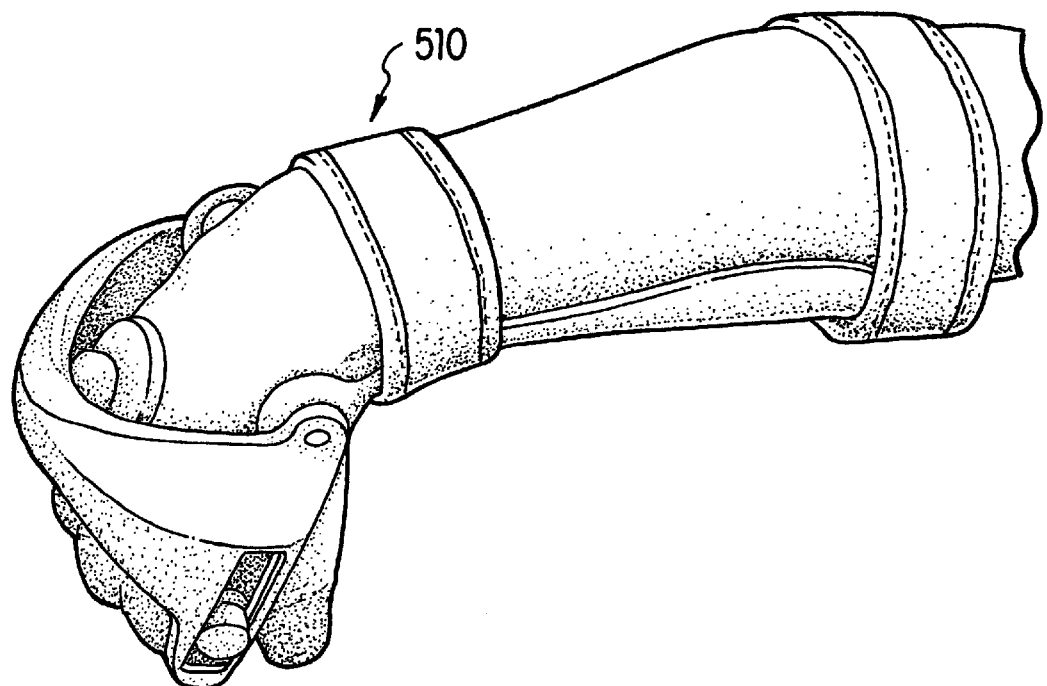
FIG. 4 shows a oblique view of the first embodiment according to the present invention with the user's wrist flexed.

The wrist brace 510 of the present invention is shown in use in FIGS. 1–5. In FIG. 1 a dorsal view looking palmarly is depicted and FIG. 2 shows a lateral view. FIG. 3 shows a palmar view, looking dorsally, while FIG. 4 shows an oblique view with the wrist flexed.

A side view of the wrist brace 510 of FIGS. 1–4 is shown in FIG. 5. As seen in FIG. 5, a forearm assembly 520 fixes the hand assembly 540 to a user's hand, wrist and forearm (not shown) and provides a hinge 541 to allow movement of the hand assembly 540 relative to the arm assembly 520 and flexion/extension motion at the wrist.

The arm assembly 520 receives the volar surface of the user's forearm. The forearm assembly 520 includes a forearm pad 522, two Velcro® fasteners 524, 526 and two Velcro® straps 528, 530. The forearm pad 522 is preferably formed from a plastic material, is generally shaped to match the contour of the forearm, and includes two rounded tabs 532, 534 which extend dorsally and are oriented perpendicular to the palmar plane. The forearm pad 522 is substantial rigid and may also include a resilient material for cushioning purposes, including at least one layer designed for comfort and transmission of moisture away from the user. A suitable material could include a cotton or similar synthetic material covered with a breathable fabric, e.g., a Gore-Tex® fabric.

At the center of each tab 532, 534, a short cylindrical stud 536 protrudes. These studs 536 mate with matching holes 542 in the hand assembly 540 so as to provide rotation of the hand assembly 540 about the studs 536, thereby permitting wrist motion by the user. The palmar support 550 (FIG. 5A), includes a threaded sleeve 551 for receiving a threaded shaft 552, and an outer cushioning layer 558. The support 550 has opposite ends 551, 552 slidably received in slots 554 and grooves 556 therein. The ends of the support 550 are configured to have an outer diameter that is greater than the width of the open slot, but smaller than the width of the groove which extends on opposite sides of the slot.

Figure 8:
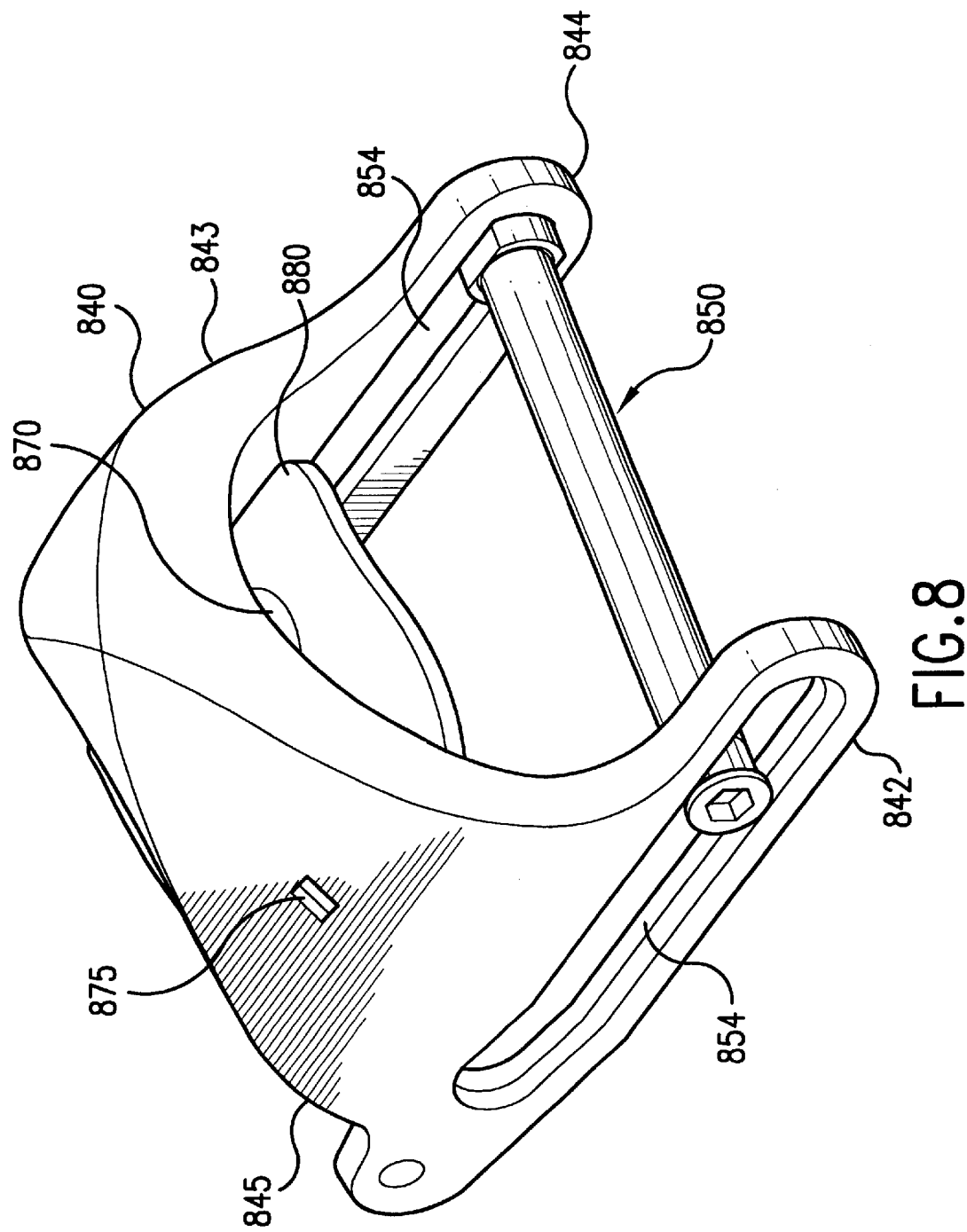
FIG. 8 shows a hand assembly embodiment of the present invention using strain gages.

In the embodiment of FIG. 8, hand assembly 840 includes sides 843 and 845 terminating in free ends 844 and 842 respectively, each of which includes a slot 854 for receiving the palmar support bar 850. The hand assembly 840 includes strain gages 875 which are positioned on opposite sides 843 and 845 of the hand assembly 840 to measure the strain generated by the dorsum support 880 and the torque nut 870. The strain gages will produce an electronic signal for processing which will be indicative of the forces applied to the dorsum of the hand in the palmar direction.

Figure 9:
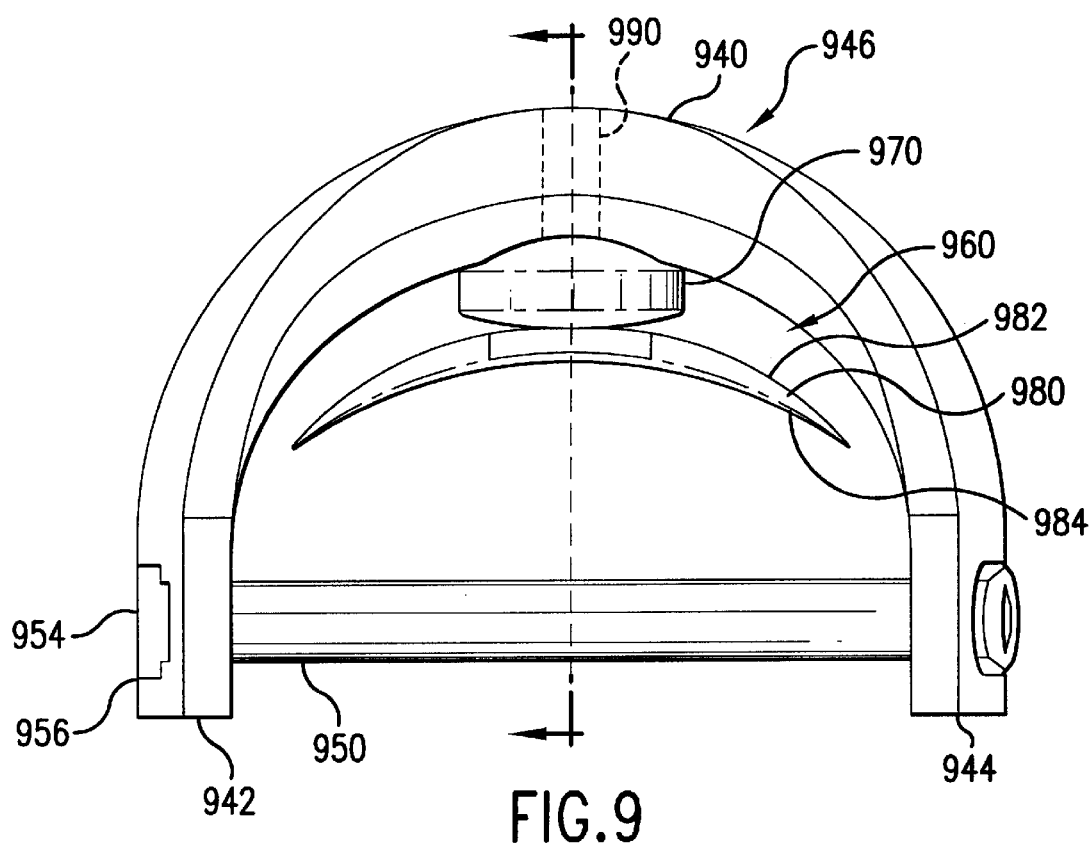
FIG. 9 is a front view of another embodiment of the present invention.

FIG. 9 provides one embodiment of the present invention showing a hand assembly 940 which applies a variable palmer force to the dorsum of the hand, which also resists that force with the distal metacarpal row, allows wrist motion, and adjustably fits different hand sizes.

The variable palmar force is applied through a variable force applicator system 960 which is positioned within the housing 946 of the hand assembly 940, which is substantially the same structure 540 shown in FIG. 5, and which includes free ends 942 and 944, each having a slot and groove, as shown in FIG. 5, for slidably supporting the palmar support 950. The variable force applicator system 960 includes a torque knob 970 and dorsal pad 980.

The variable palmar force system 960 includes the torque knob 970 and the dorsal pad 980 which includes an upper, substantially rigid polymeric member 982 and a lower cushioning member 984 for contacting and engaging the user's hand.

Figure 10:
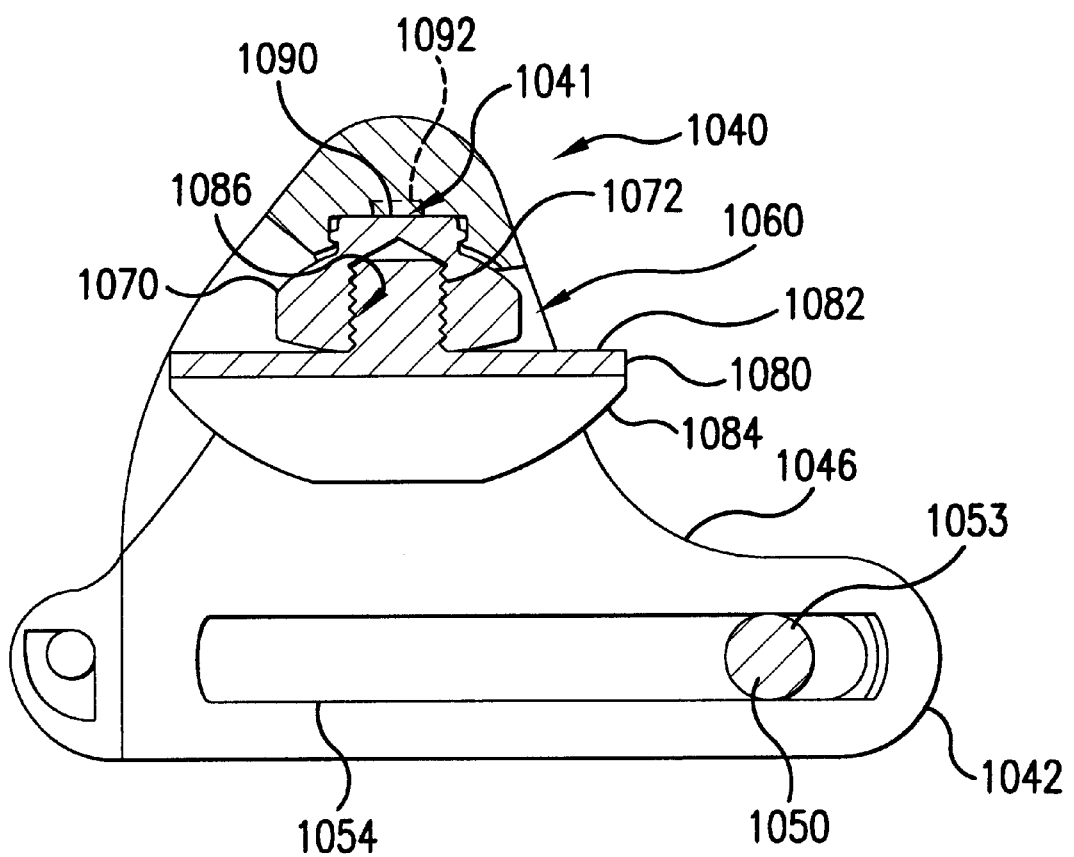
FIG. 10 is a cross-sectional side view of a further embodiment of the present invention.

A more detailed view of the force applicator system can be seen in FIG. 10. Hand assembly 1040, includes a free end 1042 with slot 1054 for receiving the palmar support 1050. The hand assembly 1040 includes a housing 1046 and a pressure applicator system 1060. Pressure applicator system 1060 includes a torque knob 1070 and a two piece dorsal pad 1080 which will contact the dorsum of the hand includes plastic component 1082 and a padding 1084. Plastic component 1082 contains a threaded cylinder 1086 extending upwardly from the back of the dorsal pad 1080 and which is received in the threaded hole 1072 in torque knob 1070. The torque knob 1070 which receives the dorsal pad 1080 and connects to the hand assembly 1040, is round in shape. Although the torque knob 1070 is shown as having a round shape, other configurations are also possible, such as pentagonal, hexagonal, etc. The torque knob 1070 is free to rotate relative to the hand assembly 1040, but the dorsal pad 1080 is not, due to contact with the user's hand. As a result of this relationship, when the torque knob 1070 is rotated, it causes translation of pressure to the dorsal pad 1080 in a dorsal to palmar direction, thus enabling direct loading or unloading of the dorsum.

The palmar bar 1050 attaches to the hand assembly 1040 and counters the dorsal load at the distal metacarpal row. The palmar bar 1050 is generally cylindrical and rides in two matching slots 1054 on the hand assembly 1040. The slots 1054 allow the palmar bar 1050 to be adjusted to a variety of hand sizes. It also accommodates left or right hands in the same components. The palmar bar 1050 includes two pieces, a threaded head and shaft, similar to that shown in FIG. 5A, forming respective ends 1053. As with FIG. 5A, bar 1050 includes a shaft which is inserted through one slot 1054 of the hand assembly 1040. The palmar support 1050 is padded to provide comfort.

The present invention provides a hand assembly which provides automatic feedback on the amount of force applied to fix the fracture, with the intent that the displacement force can be adjusted so as to generate the appropriate amount of force. The force information can be measured in a variety of ways, including pressure transducers or strain gages. For example, the hand assembly 1040 includes a force sensing resistor (FSR) transducer 1090 which is located in channel 1092 which is recessed in surface 1041 of housing assembly 1040. The sensor 1090 measures the forces exerted on the sensor 1090 by the torque knob 1060 and generates an electrical signal representative of that value.

The operation of the hand assembly 1040, shown in FIG. 10, is best described with reference to the flow charts of FIGS. 6 and 7.

Figure 6:
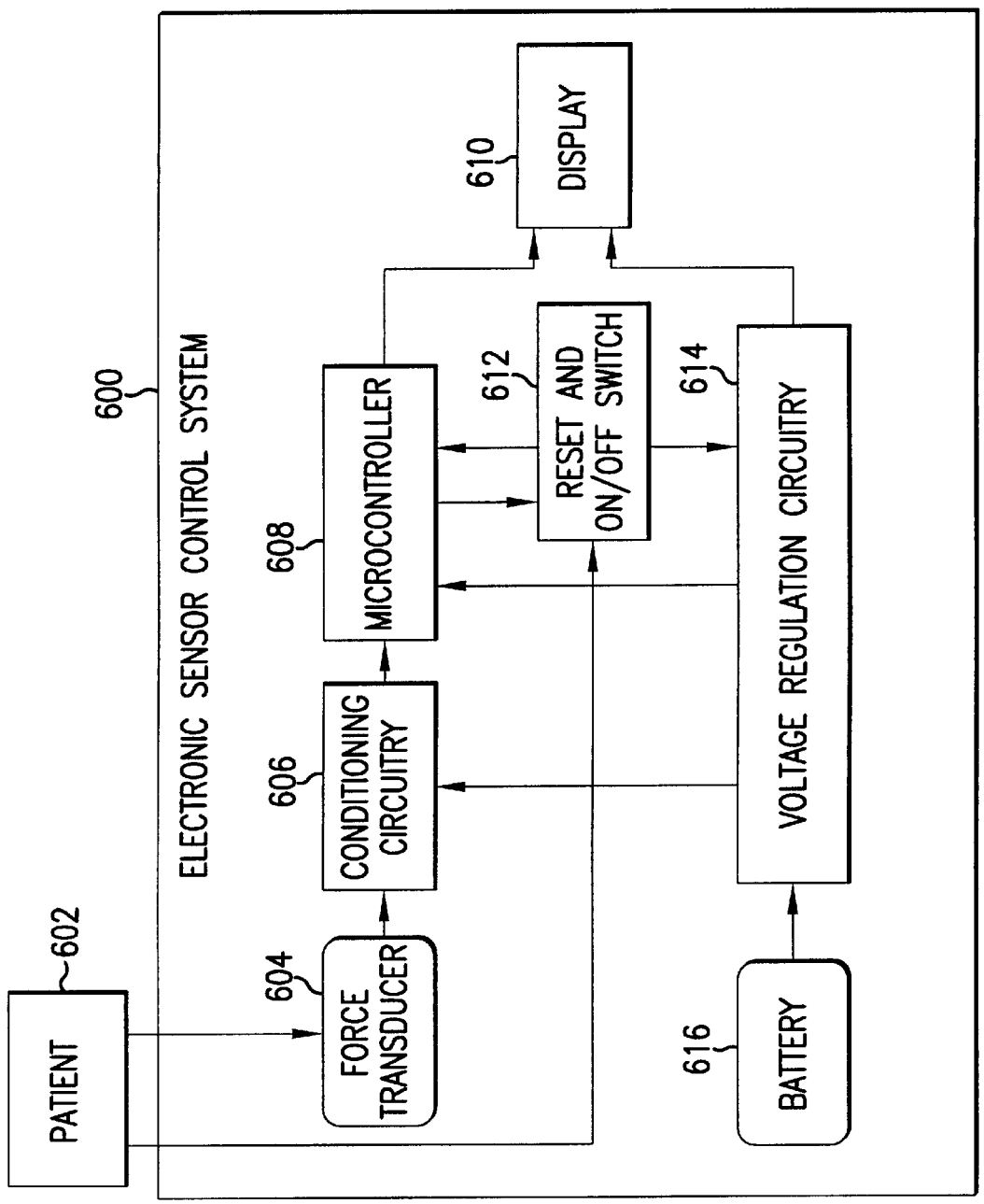
FIG. 6 is a flow chart of an electronic sensor control system "ESCS" according to the present invention.

Referring to FIG. 6, a block diagram of an Electronic Sensor Control System ("ESCS") 600 is illustrated. The ESCS 600 interfaces with a patient 602 in conjunction with the dynamic wrist brace (FIG. 1 and the hand assembly of FIGS. 8, 9, 10 and 17). A force transducer 604 (1090 of FIG. 10) is connected to a patient 602 via the wrist brace and senses the force currently applied at the force transducer location. Multiple force transducers 604 can be used. Force transducers 604 include piezoelectric transducers and force sensing resistors. One of ordinary skill in the art practicing the invention described herein could select a suitable sensor.

The force transducer 604 transmits an electronic signal, which represents the detected force, to a conditioning circuitry 606. The conditioning circuitry 606 receives the electronic signal representing the force detected by the force transducer 604 and processes the signal and then transmits a signal to a microcontroller 608.

The microcontroller 608 receives the conditioned electronic signal from the conditioning circuitry 606 and converts the signal to a signal appropriate to drive a display 610. The display 610 indicates a value that corresponds to the forces sensed by the force transducer 604. The value can be displayed in a human readable format.

A voltage regulation circuitry 614 provides regulated voltage levels to various devices including the conditioning circuitry 606, the microcontroller 608, and the display 610. The voltage levels required for each of these devises may vary. The voltage regulation circuitry 614 receives DC power from a battery 616. The battery 616 may include several batteries connected together. The voltage regulation circuitry 614 converts the voltage level of the battery 616 to the appropriate voltage levels for the various devices.

A "reset and on/off" switch 612 provides reset and on/off functions. The patient 602 or medical personal can reset the ESCS 600 by pressing a reset switch 612. The switch 612 can provide automatic resetting of the ESCS 600 at power on or during operation. The switch 612 can be used to power the ESCS 600 off or on.

Figure 7:
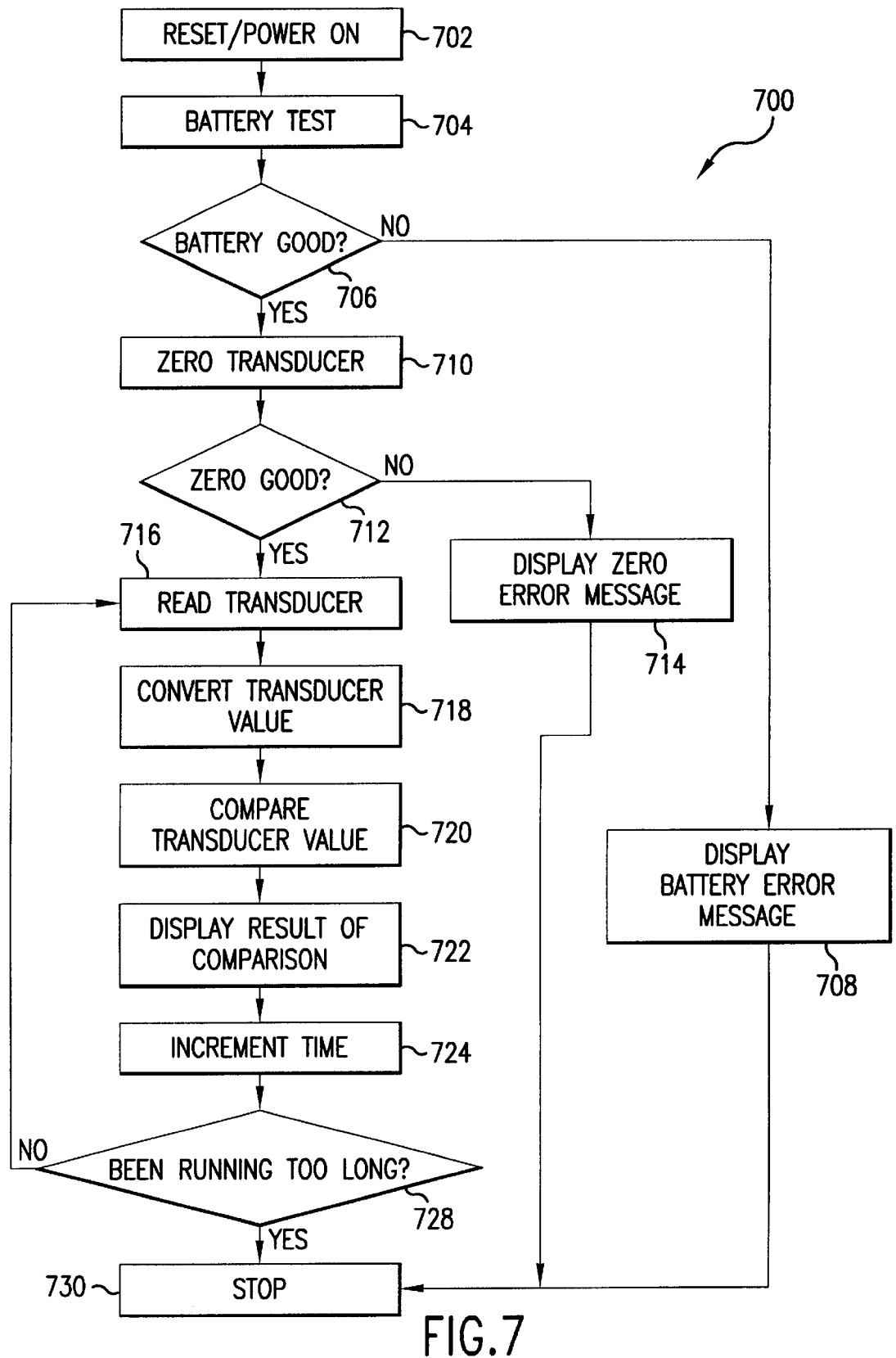
FIG. 7 is the protocol for the ESCS system according to the present invention.

Referring to FIG. 7, a flow diagram 700 of the operation of the electronic sensor control system ("ESCS") 600 is illustrated. When the ESCS is reset or the power is first turned on, the process is restarted at step 702. Then, a battery test 704 is performed to determine the status of the battery or batteries 616 (FIG. 6). If the results of the battery test is determined to be unsatisfactory in step 706, then a battery error is transmitted to the display 610 in step 708 and the ESCS is stopped in step 730.

If the result of the battery test is determined to be satisfactory in step 706, then the force transducer 604 (FIG. 6) is tested. To test the force transducers 604 the load is taken off the brace and the transducer value is set to a value of zero in step 710. In step 712, the output value of the force transducer is compared to the expected value of zero. If the output of the force transducer 604 does not match the expected value, an error message is displayed in step 714, then the ESCS is stopped in step 730.

If the battery 616 (FIG. 6) and force transducer 604 (FIG. 6) pass the initial testing, the ESCS enters a run-time processing loop including steps 716 through 728. The ESCS exits the run-time processing loop only if the timer runs out or the ESCS is reset or powered off.

In step 716, the force transducer 604 is read. The value corresponds to detected pressure at the location of the force transducer 604. In step 718, the output of the force transducer is converted to a value that corresponds to known transducer values, that is, the value can be normalized, scaled, or converted to logarithms or otherwise converted. In step 720, the converted value of the transducer reading is compared to known values. In step 722, the result of the comparison is displayed on the display 610 (FIG. 6). After the result of the comparison is displayed, the timer is incremented in step 724. Then, the timer is compared to a time-out value in step 728. If the timer exceeds the time-out value, the ESCS exits the run-time processing loop and stops in step 730. If the timer does not exceed the time-out value, the ESCS loops back to step 716 and repeats the run-time processing loop described above. While any electrical sensor will use basically the same electronics and computer software, the integration of the electrical sensor into the device may change.

Figure 17:
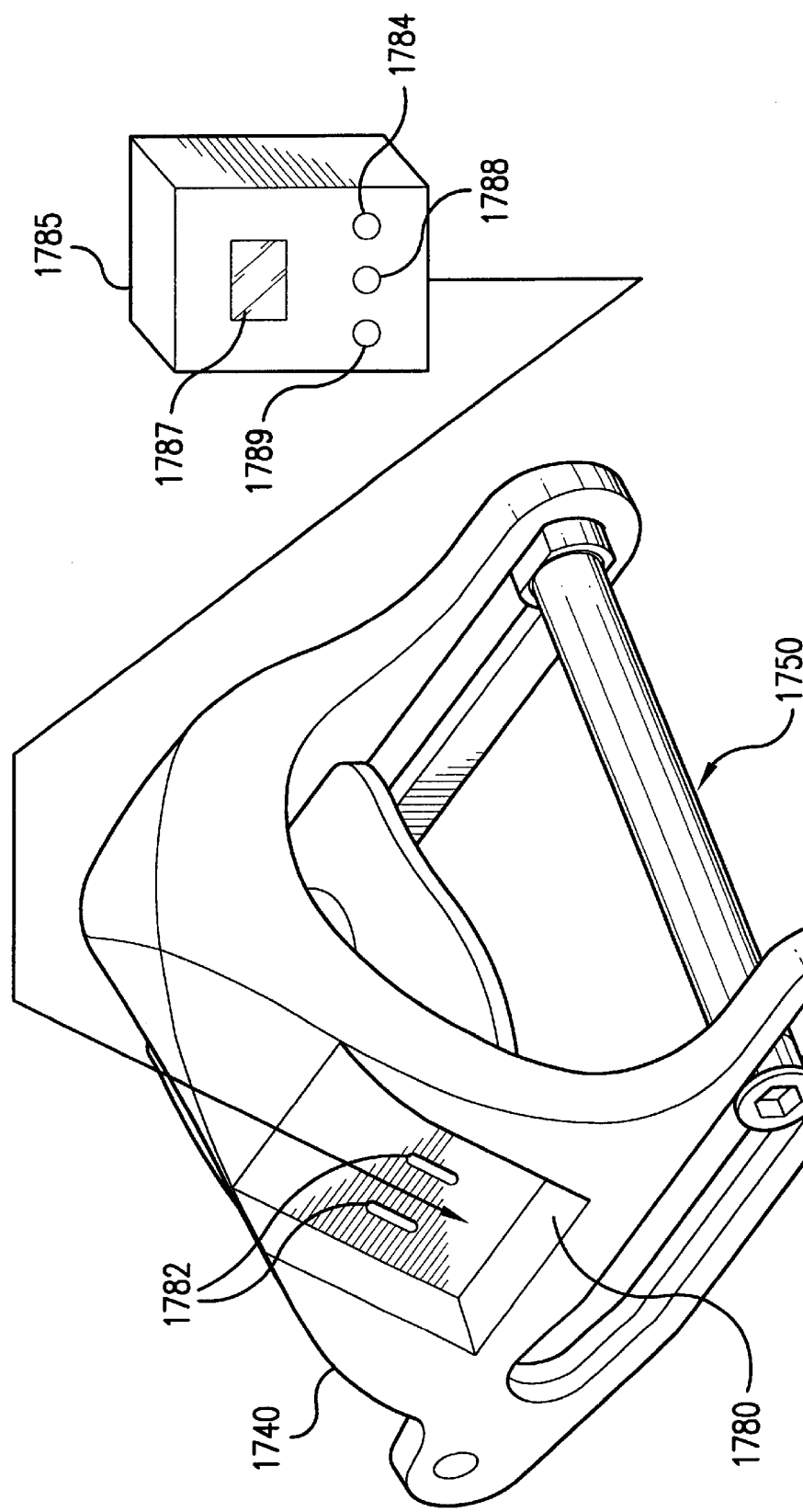
FIG. 17 is an exploded perspective view of a hand assembly and insertable computer module incorporating the components and protocol of FIGS. 6 and 7.

In FIG. 8, the strain gages 875 are used to sense the force. Leads from these gages (not shown) can be connected to the electronics described above and processed in the same manner. Alternatively, as seen in FIG. 17, the hand assembly 1740 includes a slot 1780 and electrical contacts 1782. These contacts are electrically connected to the particular sensor included in the hand assembly 1740. A removable, battery powered computer module 1785, including a variable display 1787, indicator 1784 and mode and control buttons 1788 and 1789, and including the components of FIG. 6, and capable of following the protocol of FIG. 7, is inserted into the slot 1780, thereby having terminals on the backside of module 1785 which engage contacts 1782. The circuitry for the computer module are commercially available and do not form part of the present invention.

In a further embodiment of the present invention, the torque needed to turn the torque knob 870, 970, 1070 is measured with a torque wrench (a conventional mechanical device that typically has a needle that moves dependent on torque). The scale on the face of the torque wrench would display axial force, based on a known relationship between torque and force. In this embodiment, an opening 990 would be provided in a side wall of the assembly 940 so that the torque wrench could engage torque knob 970.

Figure 11:
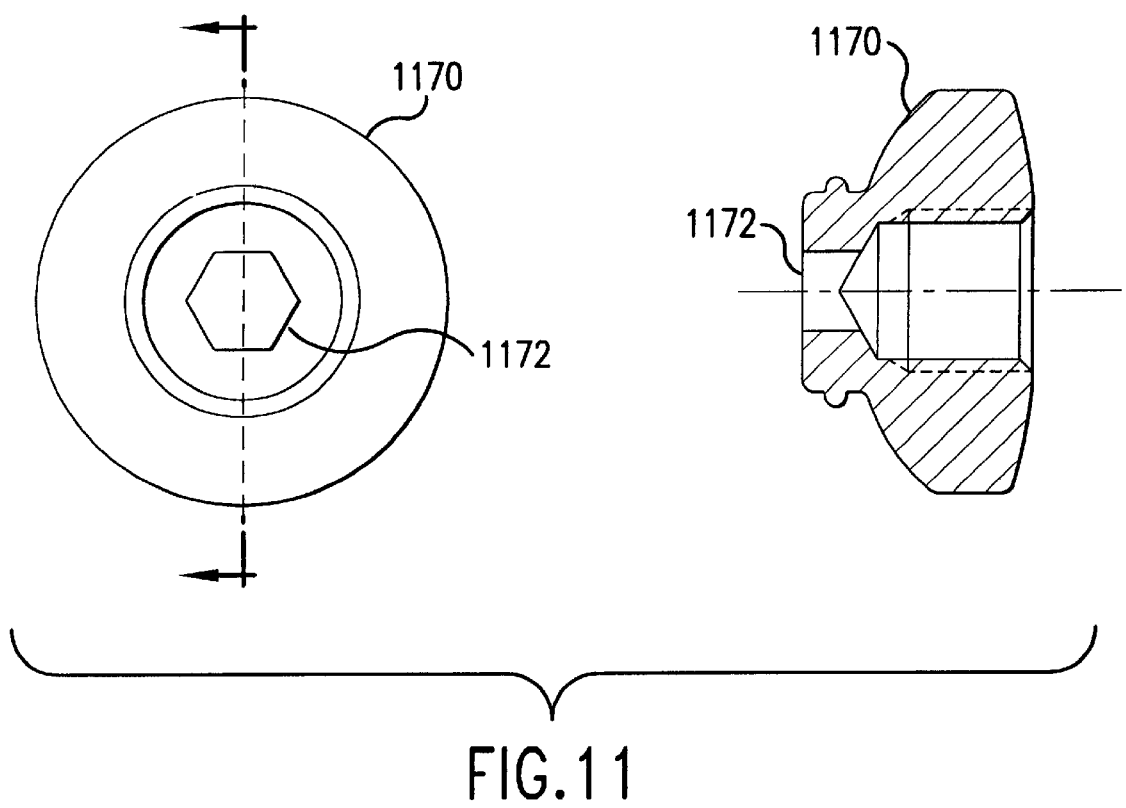
FIG. 11 is a top and side view of one torque knob embodiment of the present invention.

Alternatively, the torque knob 1170 could be modified, as shown in FIG. 11, to accommodate a standard driver at opening 1172 that would connect to the torque wrench. The housing would also need an access opening, such as opening 940 of FIG. 9 to permit adjustment of the torque knob.

Figure 18:
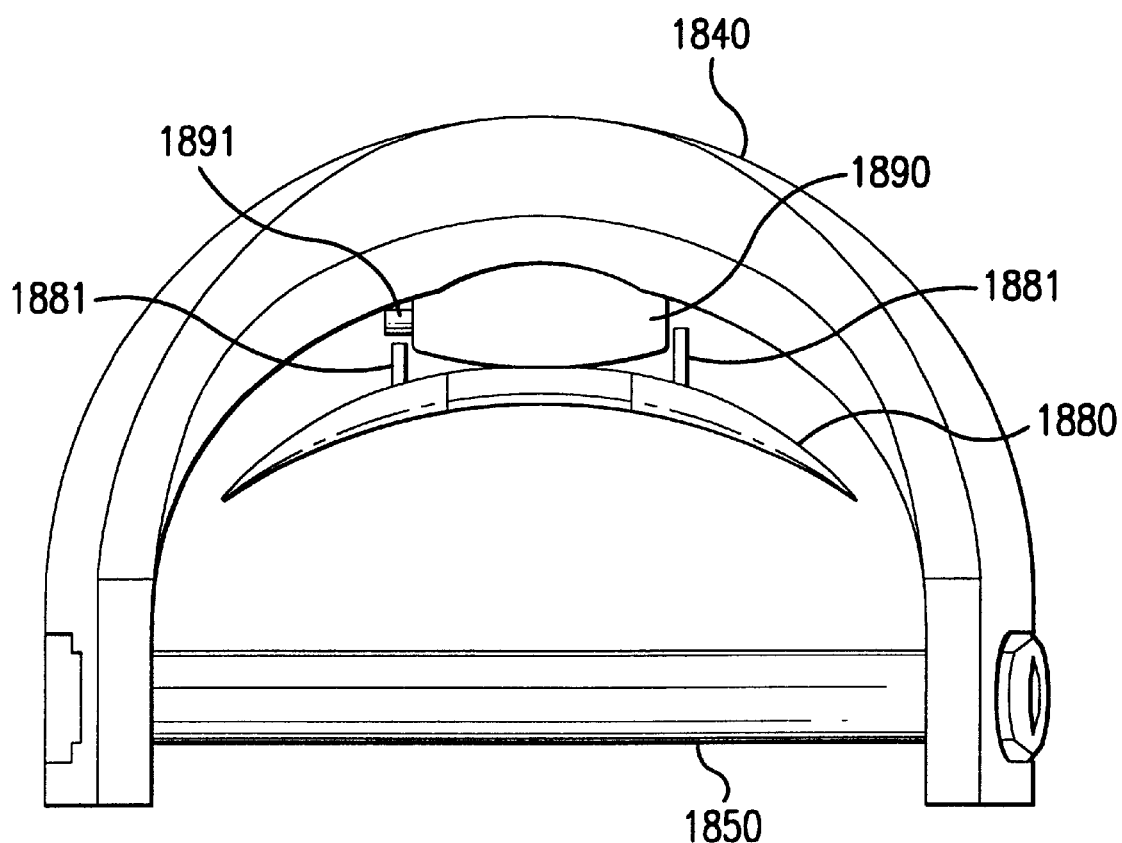
FIG. 18 is a side view of the bladder hand assembly device according to the present invention.

A still further embodiment of the present invention is schematically shown in FIG. 18. A hand assembly 1840, includes a palmar bar 1850, a bladder 1890, and fluid connector 1891 for inflating or deflating bladder 1890. The dorsal support 1880 includes an upstanding wall 1881 that circumscribes and retains the bladder in position. A sensor (not shown) is positioned between the underside of the housing and the upper surface of the bladder 1890, and would also be connected to a pressure gage to help regulate the pressure. The leads from the sensor may be connected to the electrical contacts in the hand assembly wall, as shown in FIG. 17, or connected to an appropriate control and monitoring system as discussed above.

An access hole would be provided in a sidewall of the hand assembly 1840 so that either a hand pump, such as the kind used to pump up athletic equipment, could be connected to the bladder 1890 to increase the force of the bladder by injecting more air, or the pressure of the bladder could be reduced by bleeding air from the bladder. One of ordinary skill in the art practicing the invention described herein could select a suitable sensor as the sensor in this embodiment.

A still further embodiment is using a piezoelectric transducer which could be used to detect load and provide a signal to the electronic/computer system. The mechanical embodiment of this would be identical to that for the system of FIG. 10 described above. The piezoelectric wafer would be sandwiched between the hand piece and the torque knob. Wire leads coming off of the wafer would lead to the electronics/computer system or the electrical contacts 1782.

Figure 12:
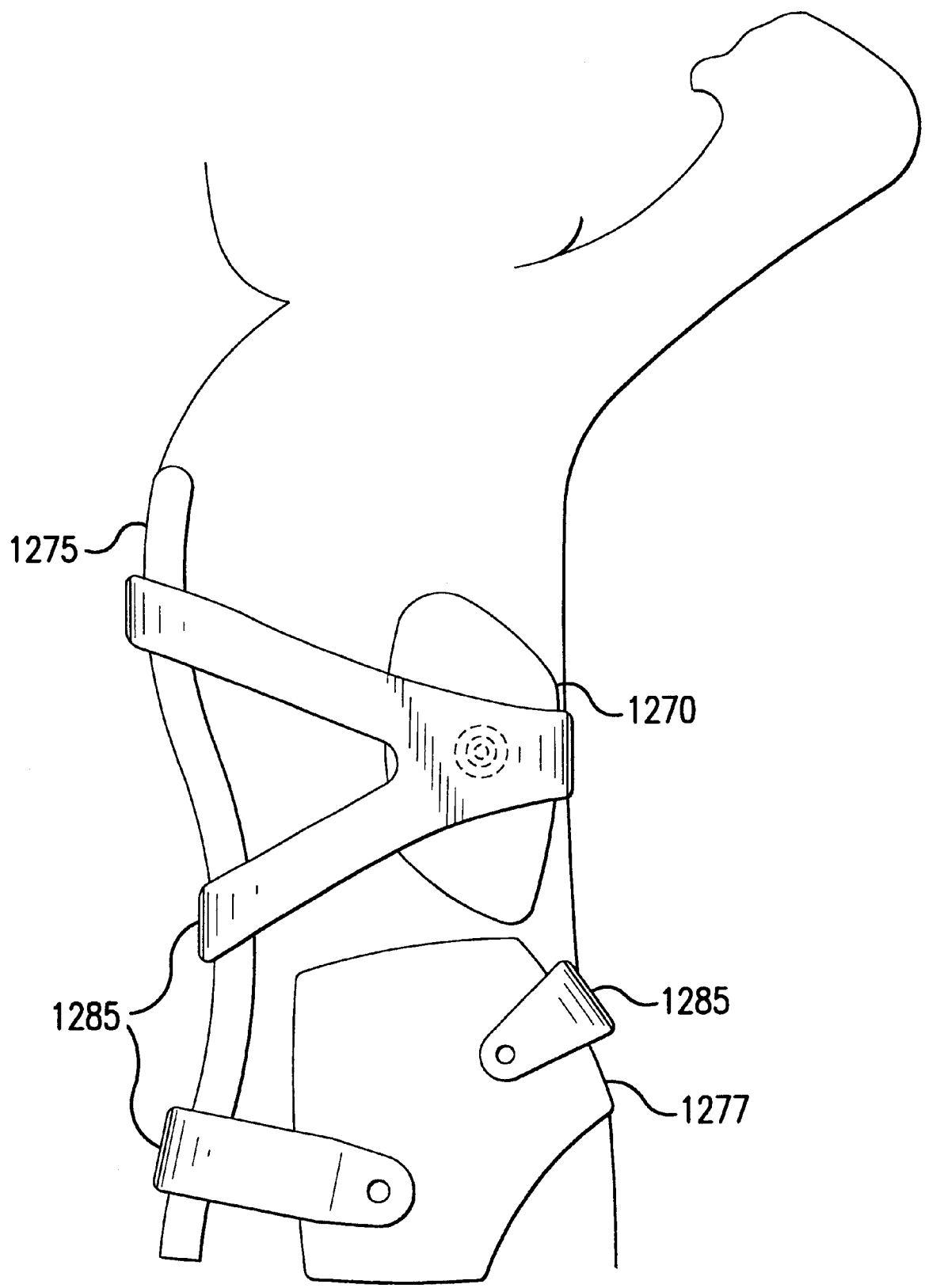
FIG. 12 is a side view of a back brace according to the present invention.
Figure 13:
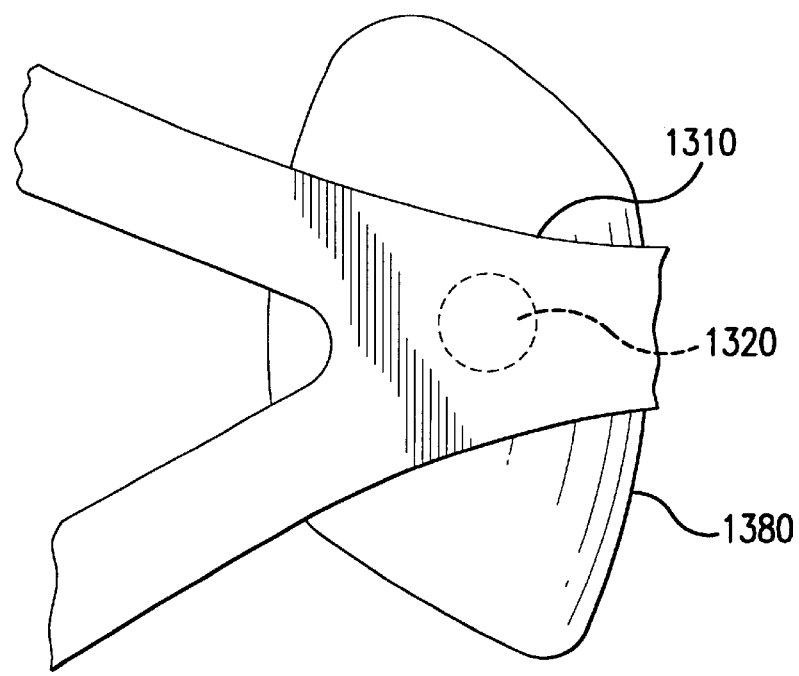
FIG. 13 is front view of the rib/torso support of the invention shown in FIG. 12.
Figure 14:
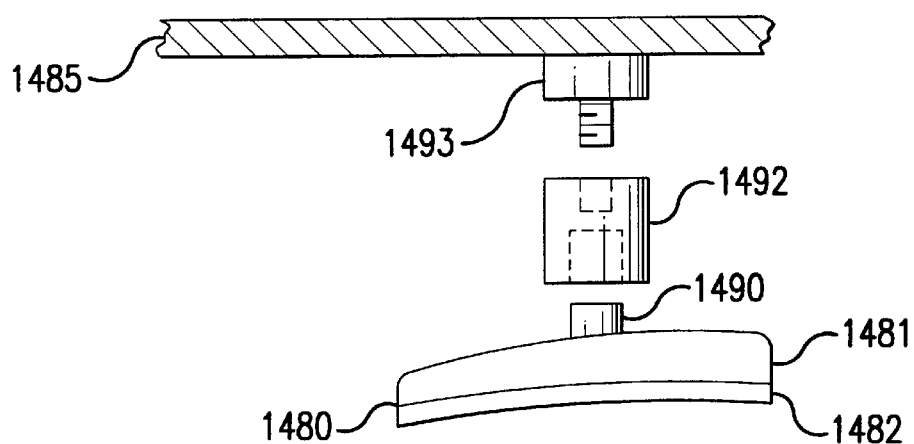
FIG. 14 is a side view of the support shown in FIG. 13.

The concept of applying a variable force via a moving actuator to the human body while providing feedback to the user regarding the force magnitude can also be applied to other braces. For example, the present invention can also be incorporated into scoliosis braces which are used to maintain, or sometimes reduce, curvature of the spine. This is accomplished by applying loads to counter the ongoing curvature. The force is developed in part by the shape of the brace and in part by the tightness of the connections. One version of this brace is shown in FIG. 12. Applying the variable force/feedback concept, the force is varied on the loading pad 1270. This force is in-part generated/tensioned by strap attachments 1285 to the support pad 1275, and the hip pad 1277. A more detailed view of how the force is varied on the loading pad is conveyed in FIG. 13 where the pressure loading pad 1380, which corresponds to pad 1270 of FIG. 12, includes a sensor and force applicator 1320. The sensor and force applicator 1320 are shown in cross-section in FIG. 14. The mechanics of this embodiment are similar to that in the palmar load on the wrist brace embodiments discussed above. A loading pad 1480 with a foam cushion 1482 contacts the skin of the subject. On the top surface of the pad 1480 is a threaded cylinder 1490. This mates with a tension knob 1492 (analogous to the torque knob of the wrist brace). A load piece 1493 is attached to the strap 1485. The sensor would rest on the end of the load piece nearest to the tension knob. As the knob 1490 is turned it would move either towards the loading pad 1480 or away from it. This movement would either decrease or increase the tension in the strap 1485. The change in tension will result in a different force on the load piece, which would be detected by the sensor.

Figures 15, 16:
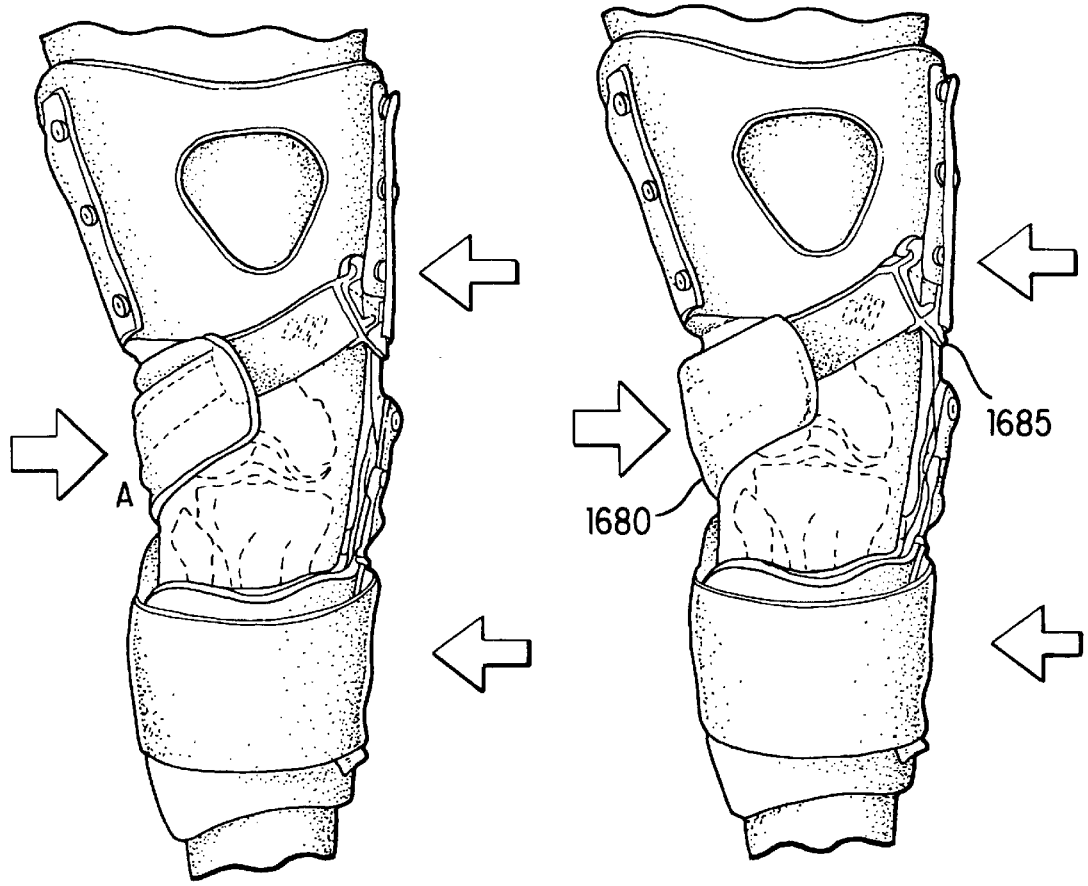
FIGS. 15 and 16 are respectively front views of a current knee brace and a knee brace in accordance with the present invention.

FIG. 15 shows a knee brace which is currently gaining popularity for nonoperative treatment of knee arthritis. The brace of FIG. 15 is shown modified in FIG. 16. in accordance with the present invention. The brace angularly displaces the femur relative to the tibia to take the load off of a condyle. Using the variable force/feedback concept of the present invention, a load pad 1680 replaces part of the strap 1685. The assembly would then have a cross-sectional view similar to that shown in FIGS. 13 and 14. The geometry of the pad and strap would be similar to that described in FIG. 12.

It will be readily appreciated that the invention in its broader aspects is not limited to the specific embodiment herein shown and described. Rather, variations may be made therefrom within the scope of the accompanying claim without departing from the principles of the invention and without sacrificing its chief advantages.

What is claimed is:

1. A brace comprising:
a first support member having inner and outer facing surfaces;
a second support member having an inner facing surface;
a support structure mounting said first and second support members so that said inner surface of said first support member faces said inner surface of said second support member, said support structure being adapted to be pivotally attached to a third support member;
a variable force applicator positioned between said outer facing surface of said first support member and said support structure to apply an amount of a variable force in a direction towards said second support member; and
an indicator displaying said amount of applied force.

2. The device of claim 1, wherein said force applicator is inflatable.

3. The brace according to claim 2, wherein the indicator displays the amount of pressure in the inflatable.

4. The device of claim 1, wherein said force applicator is mechanically adjusted.

5. The device of claim 1, wherein said indicator includes a sensor positioned between said force applicator and said support structure.

6. The device of claim 1, wherein said indicator includes a strain gage associated with said support structure.

7. The device of claim 1, wherein said indicator includes a torque wrench.

8. The device of claim 1, wherein said first support member is a dorsal support.

9. The device of claim 1, wherein said second support is a palmar support.

10. The device of claim 1, wherein said support structure is configured to receive a user's hand.

11. The device of claim 10, wherein said support structure terminates in free ends for slidably mounting said second support member.

12. The device of claim 11, wherein said free ends respectively include slots for receiving respective ends of said second support member.

13. The device of claim 11, wherein said indicator is mounted within said support structure.

14. The device of claim 13, further including a third support member configured to receive a user's arm and pivotally attached to said support structure.

15. The device of claim 14, wherein said third support member is configured to receive a volar surface of a user's forearm.

16. The device of claim 11, further including a third support member configured to receive a user's arm and pivotally attached to said support structure.

17. The device of claim 16, wherein said third support member includes at least one flexible and adjustable fastener to attach said third support to a user's arm.

18. The device of claim 1, wherein the support structure comprises a housing terminating in free ends for supporting said second support member.

19. The device of claim 1, wherein said indicator further includes a sensor for sensing said amount of force and generating a signal therefor.

20. The device of claim 19, wherein said indicator further includes a power source.

21. The device of claim 20, wherein said indicator further includes a processing circuit for receiving and processing said generated signal.

22. The device of claim 21, wherein said processing circuit receives and processes a status signal from said power source.

23. The device of claim 1, wherein said indicator includes a display for indicating said amount of force.

24. The device of claim 1, wherein said indicator includes a display for indicating power source status.

25. The device of claim 1, wherein said first support member is formed from a synthetic material.

26. The device of claim 1, wherein said support structure comprises straps for positioning said first and second support members about a user's knee.

27. The brace according to claim 1, wherein the indicator is removable.

28. The brace according to claim 1, wherein said first support is a pad configured to apply force to the metacarpals and distal carpus to align radius fractures.

29. A brace comprising:
a first support member having at least one section each of which has an outer surface;
a second support member having at least one section each of which has an outer surface;
releasable strapping affixed to said first and second support members;
a variable force applicator positioned between said outer surface of said first support member and said strapping to increase or decrease tension of said strapping; and
an indicator for displaying an amount of force applied by said first support member to said strapping.

30. The brace according to claim 29, wherein said first support member includes two sections.

31. The brace according to claim 30, wherein said member includes two sections respectively configured to fit a right and left rib/torso of a user.

32. The brace according to claim 29, wherein said second support member includes two sections.

33. The brace according to claim 32 wherein said member includes two sections attached to said strapping and configured to a back of a user.

34. The brace according to claim 29, wherein the indicator is removable.

35. The brace according to claim 29, wherein said force applicator is inflatable.

36. The brace according to claim 35, wherein the indicator displays the amount of pressure in the inflatable.

37. The brace according to claim 29, wherein said first support is a pad configured to apply force to the metacarpals and distal carpus to align radius fractures.

38. A brace comprising:
a first support member configured to fit a part of a user's limb and being connected to releasable strapping for attaching to the user;
a variable force applicator associated with said first support member to increase or decrease pressure to the user by said support member;
said applicator applying a force substantially perpendicular to said user's limb; and
an indicator for displaying an amount of said force applied by said first support member to the user.

39. The brace according to claim 38, wherein said first support is a pad configured to apply pressure to a knee of the user.

40. The brace according to claim 38, wherein said first support is a pad configured to apply pressure to an elbow of the user.

41. The brace according to claim 38, wherein said first support is a pad configured to apply pressure to a dorsum of the user.

42. The brace according to claim 38, wherein the indicator is removable.

43. The brace according to claim 38, wherein said force applicator is inflatable.

44. The brace according to claim 43, wherein the indicator displays the amount of pressure in the inflatable.

45. The brace according to claim 38, wherein said first support is a pad configured to apply force to the metacarpals and distal carpus to align radius fractures.

46. A brace comprising:
a first support member having inner and outer facing surfaces;
a second support member having an inner facing surface;
a support structure mounting said first and second support members so that said inner surfaces face one another;
a third support member configured to receive a user's forearm which is pivotally attached to said support structure;
a variable force applicator positioned between said outer supporting surface of said first support member and said support structure to apply an amount of a variable force in a direction towards said second support member; and
an indicator displaying said amount of applied force.

47. The brace according to claim 46, wherein the indicator is removable.

48. The brace according to claim 46, wherein said force applicator is inflatable.

49. The brace according to claim 48, wherein the indicator displays the amount of pressure in the inflatable.

50. The brace according to claim 46, wherein said first support is a pad configured to apply force to the metacarpals and distal carpus to align radius fractures.

51. A hand brace comprising:
a hand support structure;
a first support member having inner and outer facing surfaces and mounted within said support structure for engaging an upper surface of a patient's hand;
a second support member slidably mounted within said support structure and adapted to support a palmar surface of a patient;
a variable force applicator positioned between said outer facing surface of said first support member and said support structure to apply an amount of a variable force in a direction towards said second support member; and
an indicator displaying said amount of applied force.

52. The device according to claim 51, further including a third support member pivotally attached to said support structure.

53. The brace according to claim 51, wherein the indicator is removable.

54. The brace according to claim 51, wherein said force applicator is inflatable.

55. The brace according to claim 54, wherein the indicator displays the amount of pressure in the inflatable.

56. The brace according to claim 51, wherein said first support is a pad configured to apply force to the metacarpals and distal carpus to align radius fractures.

57. A hand brace comprising:
a hand support structure;
a first support member having inner and outer facing surfaces and mounted within said support structure for engaging a dorsal portion of a patient's hand;
a second support member slidably mounted within said support structure and adapted to support a palmar portion of a patient's hand;
an inflatable force applicator positioned between outer facing surface of said first support member and said support structure to apply an amount of a variable force in a direction towards said second support member; and
an indicator displaying said amount of applied force.

58. The device of claim 57, wherein said support structure is configured to receive a user's hand.

59. The device of claim 57, wherein said support structure terminates in free ends for slidably mounting said second support member.

60. The device of claim 59, wherein said free ends respectively include slots for receiving respective ends of said second support member.

61. The device of claim 57, further including a third support member configured to receive a user's arm and pivotally attached to said support structure.

62. The device of claim 57, wherein said indicator includes a sensor positioned between said force applicator and said support structure.

63. The brace according to claim 57, wherein the indicator is removable.

64. The brace according to claim 57, wherein said force applicator is inflatable.

65. The brace according to claim 64, wherein the indicator displays the amount of pressure in the inflatable.

66. The brace according to claim 57, wherein said first support is a pad configured to apply force to the metacarpals and distal carpus to align radius fractures.

* * * * *